US012605538B2

(12) United States Patent
Wang

(10) Patent No.: US 12,605,538 B2
(45) Date of Patent: Apr. 21, 2026

(54) RADIATION-FREE HEATING PAD AND PROCESSING TECHNOLOGY THEREOF

(71) Applicant: Ying Wang, Suzhou (CN)

(72) Inventor: Ying Wang, Suzhou (CN)

( * ) Notice: Subject to any disclaimer, the term of this patent is extended or adjusted under 35 U.S.C. 154(b) by 0 days.

(21) Appl. No.: 19/324,082

(22) Filed: Sep. 9, 2025

(65) Prior Publication Data

US 2026/0007880 A1 Jan. 8, 2026

Related U.S. Application Data

(63) Continuation of application No. 18/298,919, filed on Apr. 11, 2023, now abandoned.

(51) Int. Cl.
*A61N 1/16* (2006.01)
*A61F 7/00* (2006.01)
*A61F 7/02* (2006.01)

(52) U.S. Cl.
CPC ................. *A61N 1/16* (2013.01); *A61F 7/02* (2013.01); *A61F 2007/0071* (2013.01); *A61F 2007/0244* (2013.01)

(58) Field of Classification Search
CPC .... A61F 7/007; A61F 2007/0071; A61N 1/16
See application file for complete search history.

(56) References Cited

U.S. PATENT DOCUMENTS

| | | | |
|---|---|---|---|
| 2008/0283513 A1* | 11/2008 | Ferguson, III | ....... A01K 1/0353 |
| | | | 219/217 |
| 2009/0107984 A1* | 4/2009 | Kohn | ...................... A61F 7/007 |
| | | | 219/528 |
| 2018/0280190 A1* | 10/2018 | Betkowski | ......... A41D 13/0051 |
| 2024/0157170 A1* | 5/2024 | Kaps | ................... A47G 9/0215 |

* cited by examiner

*Primary Examiner* — Kaitlyn E Smith

(74) *Attorney, Agent, or Firm* — Nicholas Makridakis

(57) ABSTRACT

A radiation-free heating pad and a processing technology thereof is provided. The radiation-free heating pad includes heating wires, a fiber layer, a flexible shielding layer, and a reinforcement layer. The heating wires are uniformly arranged on the fiber layer in a serpentine pattern, a layer of aluminum foil is arranged on each of an upper side and a lower side of the fiber layer, and the aluminum foil tightly wraps the heating wire. The flexible shielding layer is arranged outside the aluminum foil, and the reinforcement layer is arranged outside the flexible shielding layer. The radiation-free heating pad is based on the Faraday cage effect, and an electromagnetic field generated when an electric current passes through the heating wire can be effectively counteracted by a double shielding structure composed of the aluminum foil and the flexible shielding layer.

5 Claims, 1 Drawing Sheet

RADIATION-FREE HEATING PAD AND PROCESSING TECHNOLOGY THEREOF

TECHNICAL FIELD

The present disclosure relates to the technical field of heating pad technologies, and in particular to a radiation-free heating pad and a processing technology thereof.

BACKGROUND

The heating pad is a common heating device, and its core working principle involves generating heat by passing an electric current through the heating wire, thereby meeting heating needs of users in cold environments. However, an electromagnetic field is inevitably generated when the electric current passes through the heating wire, the intensity of the electromagnetic field generally varies depending on the number of coils in the heating wire and the magnitude of the electric current. In the prior art, heating pads available on the market typically generate electromagnetic radiation levels ranging from 50 mG to 100 mG. Potential health implications of prolonged close-range exposure to such electromagnetic radiation (as in a scenario where the heating pad is used throughout the night) have gradually attracted significant public concern.

At present, in related technologies and products of the existing heating pads, effective shielding solutions have not been proposed for electromagnetic radiation generated by heating wires. While some conventional shielding technologies can achieve certain electromagnetic shielding effects through metal plates or metal meshes, such materials significantly increase the weight and rigidity of the heating pad, severely affecting use comfort of the product. Additionally, the high cost of the metal materials also limits their widespread adoption in everyday heating pad products.

SUMMARY

An objective of the present disclosure is to provide a radiation-free heating pad and processing technology thereof to solve the foregoing problem.

The present disclosure achieves the foregoing objective through the following technical solution.

A radiation-free heating pad includes heating wires, a fiber layer, a flexible shielding layer, and a reinforcement layer. The heating wires are uniformly arranged on the fiber layer in a serpentine pattern, a layer of aluminum foil is arranged on each of an upper side and a lower side of the fiber layer, and the aluminum foil tightly wraps the heating wire.

The flexible shielding layer is arranged outside the aluminum foil, and the reinforcement layer is arranged outside the flexible shielding layer.

In some implementations, a grid-patterned resilient rib is arranged between the flexible shielding layer and the reinforcement layer.

In some implementations, a thickness of the fiber layer is less than a diameter of the heating wire.

In some implementations, the flexible shielding layer is at least one of conductive cloth, anti-magnetic cloth or RFID (radio frequency identification) shielding fabric.

In some implementations, the reinforcement layer is flannel or non-woven fabric, and the reinforcement layer is compounded on a surface of the flexible shielding layer.

In some implementations, an overall edge of the reinforcement layer and the flexible shielding layer is provided with a hem.

In some implementations, a surface of one side of the aluminum foil is covered with a PET (polyethylene terephthalate) film, and the aluminum foil has a thickness of 0.01-0.05 mm.

The present disclosure provides a processing technology of a radiation-free heating pad, including the following steps:

S100: laying a fiber layer flat on a workbench, dispensing adhesive along a serpentine path on a surface of the fiber layer, where a diameter of an adhesive point is 3-5 mm, and a spacing between the adhesive points is 20-30 mm; laying a heating wire along an adhesive point path in a serpentine pattern, lightly pressing to preliminarily bond the heating wire to the fiber layer, and drying and curing an adhesive layer at a low temperature, where the drying is carried out at a temperature of 40-50° C. for 10-15 minutes;

S200: compounding a PET film on a surface of aluminum foil, and placing a fiber layer fixed with the heating wire between the two layers of aluminum foil to make the heating wire completely covered within a range of the aluminum foil;

folding the aluminum foil on a lower side of the fiber layer upward to make the aluminum foil closely attached to both the bottom of the heating wire and a lower surface of the fiber layer, gently pressing with a silicone roller to expel air bubbles to achieve tight contact between the aluminum foil and the heating wire; and folding the aluminum foil on an upper side of the fiber layer downward to cover both the top of the heating wire and an upper surface of the fiber layer; and rolling with the silicon roller to make the aluminum foil completely wrap the heating wire and fiber layer; and S300: laying a flexible shielding layer flat on the workbench, placing the aluminum foil compounded with the PET film at the center of the flexible shielding layer, bonding the flexible shielding layer to the aluminum foil by hot pressing, where the hot pressing is carried out at a temperature of 80-100° C. and a pressure of 0.2-0.3 MPa for 10-20 s.

The method further includes the following steps:

S400: laying grid-patterned resilient ribs at spacings of 50-100 mm in both transverse and longitudinal directions on an outer surface of the flexible shielding layer in a crisscrossing manner, where end points of the grid-patterned resilient ribs are aligned with edges of the flexible shielding layer, and the grid-patterned resilient ribs are tightly attached to the flexible shielding layer by stitching; and S500: laying a non-woven fabric reinforcement layer flat on a surface of the grid-patterned resilient rib, and integrating the reinforcement layer, the flexible shielding layer and the grid-patterned resilient ribs into a whole by hot pressing or adhesive bonding.

The method further includes the following steps:

S600: folding over 5-10 mm at an edge of the overall heating pad to form a double-layer hem, and carrying out hemming treatment by stitching.

In some implementations, in S200, the aluminum foil is subjected to oxidation treatment, the cleaned aluminum foil is immersed in a passivation solution, so that a surface of the aluminum foil reacts with the passivation solution to form a composite oxide film.

The present disclosure has beneficial effects that based on the Faraday cage effect, an electromagnetic field generated when an electric current passes through a heating wire can be effectively counteracted by a double shielding structure composed of aluminum foil and a flexible shielding layer. In addition, the heating wire is uniformly fixed onto the fiber layer in a serpentine pattern, thereby preventing localized overheating caused by displacement or accumulation of the heating wire during use or cleaning. The heat generated by the heating wire can be rapidly diffused by high thermal conductivity of the aluminum foil, and with the support of the fiber layer, the surface temperature distribution of the heating pad is more uniform and the heating comfort is improved.

The present disclosure further employs a reinforcement layer, and employs grid-patterned resilient ribs to improve tensile resistance. This design can effectively reduce frictional damage between the shielding layer and the heating wire during machine washing, and prolong the service life of the heating pad.

BRIEF DESCRIPTION OF THE DRAWINGS

To describe technical solutions in embodiments of the present disclosure or in the prior art more clearly, the following briefly introduces accompanying drawings required for describing the embodiments or the prior art. Apparently, the accompanying drawings in the following description show merely some embodiments of the present disclosure, and a person of ordinary skill in the art may still derive other drawings from these accompanying drawings without creative efforts.

Figure 1:
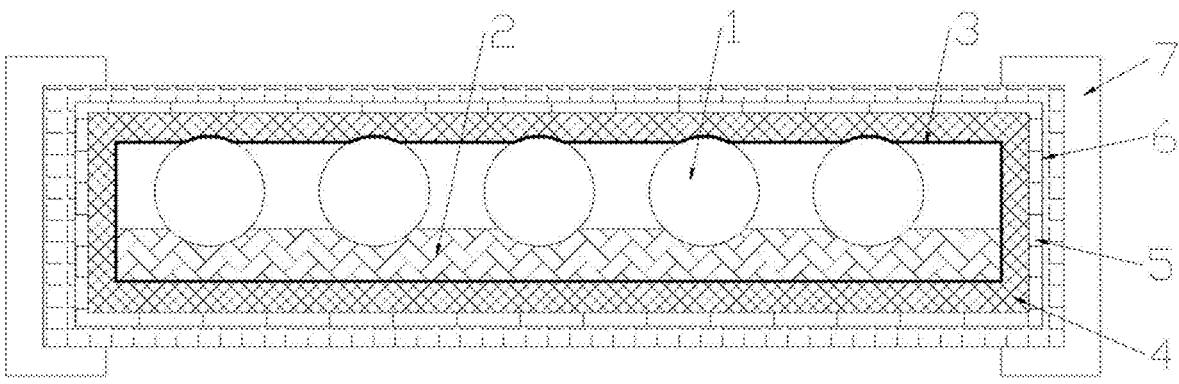
FIG. 1 is a diagram of a structure of a heating pad according to the present disclosure.

Reference numerals are described as follows:

1—heating wire; 2—fiber layer; 3—aluminum foil; 4—flexible shielding layer; 5—grid-patterned resilient rib; 6—reinforcement layer; 7—hem; 8—control module.

DETAILED DESCRIPTION OF THE EMBODIMENTS

To make the objective, technical solutions and advantages of the present disclosure more clearly, the technical solutions of the present disclosure are described in detail below. Apparently, the described embodiments are merely a part rather than all of the embodiments of the present disclosure. All other implementations obtained by a person of ordinary skill in the art based on the embodiments of the present disclosure without creative efforts shall fall within the scope of protection of the present disclosure.

Figure 2:
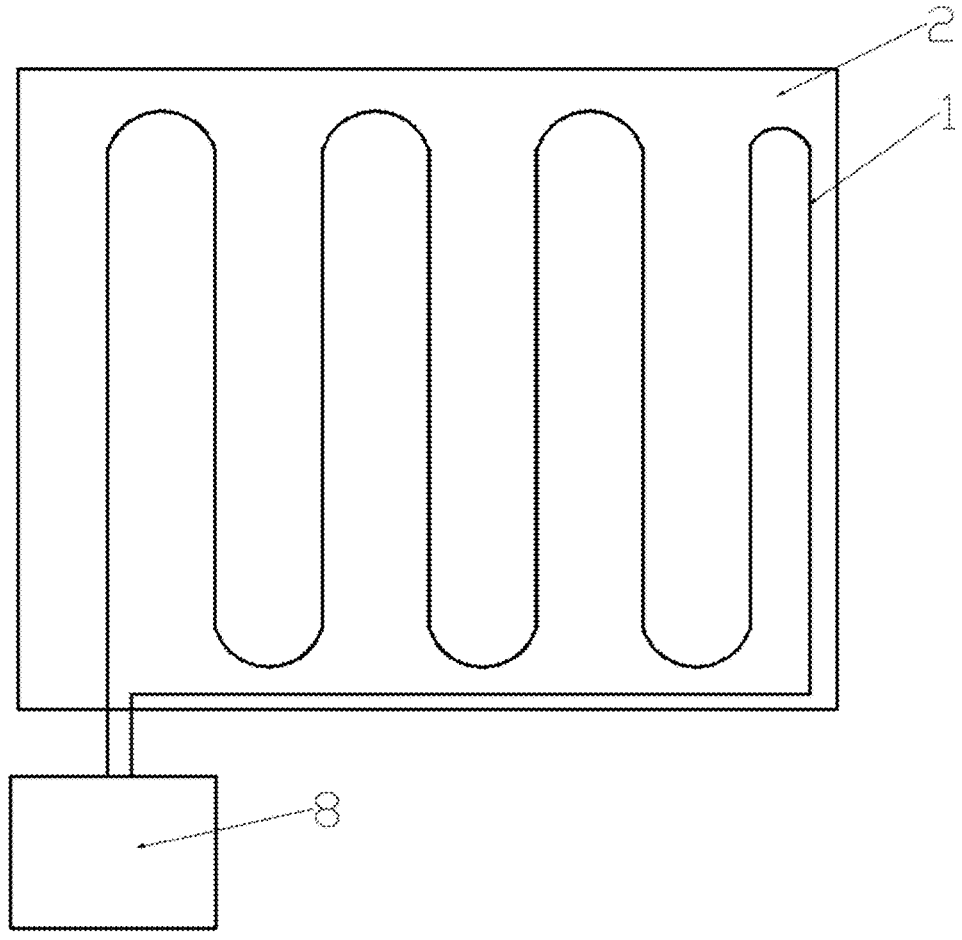
FIG. 2 is a diagram of a layout structure of a heating wire of a heating pad according to the present disclosure.

Refer to FIG. 1 to FIG. 2, the present disclosure provides a radiation-free heating pad, including a heating wire 1, a fiber layer 2, a flexible shielding layer 4, and a reinforcement layer 6. The heating wire 1 is uniformly arranged on the fiber layer 2 in a serpentine pattern, a layer of aluminum foil 3 is arranged on each of an upper side and a lower side of the fiber layer 2, and the aluminum foil 3 tightly wraps the heating wire 1. The flexible shielding layer 4 is arranged outside the aluminum foil 3, and the reinforcement layer 6 is arranged outside the flexible shielding layer 4.

The radiation-free heating pad is based on the Faraday cage effect, conductive cloth outside each heating wire 1 forms an independent shielding space, which counteracts an electromagnetic field generated by the corresponding heating wire 1 to achieve electromagnetic radiation shielding. An electromagnetic field generated when an electric current passes through the heating wire 1 can be effectively counteracted by a double shielding structure composed of the aluminum foil 3 and the flexible shielding layer 4. In addition, the heating wire 1 is uniformly fixed onto the fiber layer 2 in a serpentine pattern, thereby preventing localized overheating caused by displacement or accumulation of the heating wire 1 during use or cleaning. The heat generated by the heating wire 1 can be rapidly diffused by high thermal conductivity of the aluminum foil 3, and with the support of the fiber layer 2, the surface temperature distribution of the heating pad is more uniform and the heating comfort is improved.

The present disclosure further employs a reinforcement layer 6, and employs grid-patterned resilient ribs 5 to improve tensile resistance. This design can effectively reduce frictional damage between the shielding layer and the heating wire during machine washing, and prolong the service life of the heating pad.

Refer to FIG. 1, in this embodiment, a grid-patterned resilient rib 5 is arranged between the flexible shielding layer 4 and the reinforcement layer 6. The grid-patterned resilient rib 5 is a resilient spandex rib or polyester filament rib, and the ribs are arranged in parallel along length and width directions of the heating pad by 50-100 mm, and are fixed between two layers by stitching or hot pressing. The ribs can enhance the tensile performance of the shielding layer, thereby avoiding the deformation or cracking of the shielding layer caused by tension of the heating pad during bending and use, and maintaining the tightness of a Faraday cage.

In some embodiments, a thickness of the fiber layer 2 is less than a diameter of the heating wire 1, and the heating wire 1 protrudes from a surface of the fiber layer 2, so that the aluminum foil can completely cover and wrap the heating wire 1.

In this embodiment, the flexible shielding layer 4 is at least one of conductive cloth, anti-magnetic cloth or RFID shielding fabric. The reinforcement layer 6 is flannel or non-woven fabric, and the reinforcement layer is compounded onto the surface of the flexible shielding layer 4. The non-woven fabric may be spun-bonded non-woven fabric or spunlace non-woven fabric, which is bonded to the flexible shielding layer 4 by dot-like hot pressing or adhesive bonding. The non-woven fabric is soft and friction-resistant, and thus can reduce a direct friction between the shielding layer and the heating wire 1 during machine washing and reduce a risk of shielding coating peeling. In addition, the non-woven fabric has good air permeability and does not affect heat conduction.

In some implementations, an overall edge of the reinforcement layer 6 and the flexible shielding layer 4 is provided with a hem 7. A hem 7 structure formed by folding and fixing the edge can prevent the shielding layer, the reinforcement layer 6 and other materials from fraying, cracking or delaminating due to friction or tension during use or machine washing, thereby maintaining the integrity of each layer of structure.

In some implementations, a surface of one side of the aluminum foil 3 is covered with a PET film, and a thickness of the aluminum foil 3 is 0.01-0.05 mm. Compounding an insulating film on the surface of the aluminum foil 3 can further enhance electrical isolation between the heating wire 1 and an external structure and improve electrical safety of the heating pad.

The present disclosure provides a processing technology of a radiation-free heating pad, including the following steps.

S100: A fiber layer is laid flat on a workbench, adhesive is dispensed along a serpentine path on a surface of the fiber layer, where a diameter of an adhesive point is 3-5 mm, and a spacing between the adhesive points is 20-30 mm; a heating wire 1 is laid along an adhesive point path in a serpentine pattern, lightly pressing is carried out to preliminarily bond the heating wire to the fiber layer, and an adhesive layer is dried and cured at a low temperature, where the drying is carried out at a temperature of 40-50° C. for 10-15 minutes. In this technology, stable attachment of the heating wire 1 can be ensured, thereby preventing the heating wire from shifting and winding during use or subsequent processing, and ensuring uniform distribution of the heating wire 1.

S200: A PET film is compounded on a surface of aluminum foil 3, and a fiber layer 2 fixed with the heating wire 1 is placed between the two layers of aluminum foil 3 to make the heating wire 1 completely covered within a range of the aluminum foil 3.

The aluminum foil 3 on a lower side of the fiber layer 2 is folded upward to make the aluminum foil 3 closely attached to both the bottom of the heating wire 1 and a lower surface of the fiber layer 2, and gently pressing is carried out with a silicone roller to expel air bubbles to achieve tight contact between the aluminum foil 3 and the heating wire 1. Then, the aluminum foil 3 on an upper side of the fiber layer 2 is folded downwards to cover both the top of the heating wire 1 and an upper surface of the fiber layer 2, and gently rolling and pressing is carried out with the silicone roller to make the aluminum foil 3 completely wrap the heating wire 1 and the fiber layer 2. In this technology, the aluminum foil 3 closely wraps the heating wire 1 to form a first electromagnetic shielding barrier, which can preliminarily counteract an electromagnetic field based on Faraday cage effect. The PET film can enhance insulation and mechanical strength of the aluminum foil 3 and avoid direct conductive contact between the aluminum foil 3 and the heating wire 1. The silicone roller can expel air bubbles by rolling and ensure that the aluminum foil 3 is in close contact with the heating wire 1 and the fiber layer 2, which not only improves the heat conduction efficiency and makes the heat diffused evenly, but also ensures the continuity of shielding and prevents electromagnetic radiation from leaking from a gap.

S300: A flexible shielding layer 4 is laid flat on the workbench, the aluminum foil compounded with the PET film is placed at the center of the flexible shielding layer 4, the flexible shielding layer 4 is bonded to the aluminum foil 3 by hot pressing, where the hot pressing is carried out at a temperature of 80-100° C. and a pressure of 0.2-0.3 MPa for 10-20 s. in this technology, hot pressing parameters can ensure that the shielding layer (conductive cloth, antimagnetic cloth and the like) is closely bonded to the aluminum foil 3 compounded with the PET film, without hollowing or delamination, so that the aluminum foil 3 and the flexible shielding layer 4 cooperate to form a closed shielding space, which can enhance the shielding effect of the electromagnetic radiation, and reduce the radiation to zero.

S400: Grid-patterned resilient ribs 5 are laid at spacings of 50-100 mm in both transverse and longitudinal directions on an outer surface of the flexible shielding layer 4 in a crisscrossing manner, where end points of the grid-patterned resilient ribs 5 are aligned with edges of the flexible shielding layer 4, and the grid-patterned resilient ribs 5 are tightly attached to the flexible shielding layer 4 by stitching. The grid-patterned ribs with a spacing of 50-100 mm can disperse an external force, avoid the deformation or cracking of the shielding layer caused by tension of the heating pad during bending and use, and maintaining the tightness of a Faraday cage.

S500: A non-woven fabric reinforcement layer 6 is laid flat on a surface of the grid-patterned resilient rib 5, and the reinforcement layer 6, the flexible shielding layer 4 and the grid-patterned resilient ribs 5 are integrated into a whole by hot pressing or adhesive bonding. The non-woven fabric is soft and friction-resistant, and thus can reduce a direct friction between the shielding layer and the heating wire 1 during machine washing and reduce a risk of shielding coating peeling.

S600: An edge of the overall heating pad is folded over 5-10 mm to form a double-layer hem, and hemming treatment is carried out by stitching. The double-layer hem 7 can prevent edges of all material layers (shielding layer, reinforcement layer 6, aluminum foil 3, and the like) from fraying and delaminating, thereby avoiding direct water erosion during machine washing that could cause structural loosening.

It should be noted that in S200, to prevent the aluminum foil 3 from oxidizing, the aluminum foil 3 needs to be oxidized, the cleaned aluminum foil 3 is immersed in the passivation solution, and the surface of the aluminum foil 3 reacts with the passivation solution to form a composite oxide film, which can enhance corrosion resistance of that aluminum foil 3 and avoid oxidation failure after long-term use or machine washing, thereby prolonging the shielding life.

It needs to be further noted that the heating wire 1 of the heating pad of the present disclosure is connected to an external control module 8, and the control module 8 can control a heating temperature, heating time and the like.

The foregoing is only the specific implementation of the present disclosure, but the scope of protection of the present disclosure is not limited thereto. Any modifications or replacements that can be easily conceived by those skilled in the art within the technical scope disclosed by the present disclosure should be covered within the scope of protection of the present disclosure. Therefore, the scope of protection of the present disclosure should be based on the scope of protection of the claims.

What is claimed is:

1. A radiation-free heating pad, comprising heating wires, a fiber layer, a flexible shielding layer, and a reinforcement layer, wherein the heating wires are uniformly arranged on the fiber layer in a serpentine pattern, a layer of aluminum foil is arranged on each of an upper side and a lower side of the fiber layer, and the aluminum foil tightly wraps the heating wire; and the flexible shielding layer is arranged outside the aluminum foil, and the reinforcement layer is arranged outside the flexible shielding layer;

wherein a grid-patterned resilient rib is arranged between the flexible shielding layer and the reinforcement layer;

wherein a surface of one side of the aluminum foil is covered with a PET (polyethylene terephthalate) film, and the aluminum foil has a thickness of 0.01-0.05 mm.

2. The radiation-free heating pad according to claim 1, wherein a thickness of the fiber layer is less than a diameter of the heating wire.

3. He radiation-free heating pad according to claim 2, wherein the reinforcement layer is flannel or non-woven fabric, and the reinforcement layer is compounded on a surface of the flexible shielding layer.

4. The radiation-free heating pad according to claim 1, wherein the flexible shielding layer is at least one of conductive cloth, anti-magnetic cloth or RFID (radio frequency identification) shielding fabric.

5. The radiation-free heating pad according to claim 4, wherein an overall edge of the reinforcement layer and the flexible shielding layer is provided with a hem.

\* \* \* \* \*